(12) United States Patent
Li et al.

(10) Patent No.: US 8,288,533 B1
(45) Date of Patent: Oct. 16, 2012

(54) METHODS FOR PREPARING BENZOXAZINES USING AQUEOUS SOLVENT

(75) Inventors: Wei Helen Li, Danville, CA (US); Wenbo Jiang, Concord, CA (US)

(73) Assignee: Henkel Corporation, Rocky Hill, CT (US)

( * ) Notice: Subject to any disclaimer, the term of this patent is extended or adjusted under 35 U.S.C. 154(b) by 84 days.

(21) Appl. No.: 12/888,850

(22) Filed: Sep. 23, 2010

(51) Int. Cl.
*C07D 265/12* (2006.01)
(52) U.S. Cl. ............................................. 544/90; 544/73
(58) Field of Classification Search .................... 544/90, 544/73
See application file for complete search history.

(56) References Cited

OTHER PUBLICATIONS

Burke et al. Journal of Organic Chemistry (1964), 29(4), 909-12.*
Higham et al. Tetrahedron Letters 47 (2006), 4419-4423.*

* cited by examiner

*Primary Examiner* — Kahsay T Habte
(74) *Attorney, Agent, or Firm* — Steven C. Bauman

(57) ABSTRACT

This invention relates to syntheses for the preparation of benzoxazine, including benzoxazine monomers and benzoxazime oligomers, from phenolic compounds, aldehyde compounds, and either primary diamine compounds, such as diamino alkylene compounds, e.g., methylene diamine, or diamino arylene compounds, e.g., phenylene diamine, using water, and optionally an organic solvent, as the reaction solvent.

20 Claims, No Drawings

METHODS FOR PREPARING BENZOXAZINES USING AQUEOUS SOLVENT

TECHNICAL FIELD

This invention relates to syntheses for the preparation of benzoxazine compounds, including benzoxazine monomers and benzoxazine oligomers, from phenolic compounds, aldehyde compounds, and either primary diamine compounds, such as diamino alkylene compounds, e.g., methylene diamine, or diamino arylene compounds, e.g., phenylene diamine.

BACKGROUND

Benzoxazines of the general formula

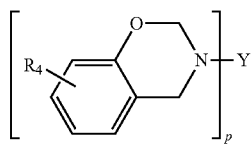

where p is 2, Y is selected from biphenyl, diphenyl methane, diphenyl isopropane, diphenyl sulfide, diphenyl sulfoxide, diphenyl sulfone, and diphenyl ketone, and R4 is selected from hydrogen, halogen, alkyl and alkenyl, are ordinarily prepared by reacting a phenolic compound, with an aldehyde compound and an alkyl amine. This reaction is known to be conducted under solventless conditions or in a solvent such as toluene, dioxane, alcohol or diethyl ether.

In U.S. Pat. No. 5,543,516 (Ishida) a method for preparing a benzoxazine compound is provided, in which a reaction mixture containing a phenolic compound, a primary amine, and an aldehyde is prepared without a separate solvent; the reactants are brought to a temperature at which the reactants combine chemically and are maintained at that temperature to reportedly form the benzoxazine compound. Ishida notes that prior art methods of forming benzoxazines require significant amounts of solvent to dissolve the reactants, leading to long reaction times. Ishida at col. 3, lines 43-52. Solventless systems require that at least one of the reactants be a liquid in order to solvate the reaction mixture. As not every reaction mixture will include a liquid reactant, solventless systems are not universally appropriate.

Chinese Patent Publication No. CN 1451679 (Gu) is directed to modified benzoxazine resins for RTM applications and discloses that in the past benzoxazine resins had been synthesized using organic solvents, such as toluene, dioxane and dimethyl benzene (citing to Chinese Patent Application No. CN 94111852.5). In the CN '679 publication, however, toluene is the only solvent used in the working examples.

Benzoxazines are presently available from several sources commercially, including Huntsman Specialty Chemicals, Brewster, New York; Georgia-Pacific Resins, Inc. and Shikoku Chemicals Corporation, Chiba, Japan, the last of which offers among others B-a, B-m, F-a, C-a and F-a benzoxazine resins.

However, these known synthetic methods and some commercial benzoxazines have shortcomings. For instance, some of the organic solvents used in the synthesis are toxic or environmentally hazardous and thus are not generally desirable for use in commercial processes. Indeed, many jurisdictions have implemented restrictions on the use of certain solvents and have even prohibited the use of particular solvents entirely. Others solvents, while deemed generally safe, must be removed using elevated temperatures that cause a degradation and/or premature polymerization of some benzoxazine compounds, resulting in compromised performance of curable compositions formulated with such benzoxazines.

The known synthetic methods usually require relatively long processing times, i.e., at least several hours, in order to perform the desired reaction, and to separate and purify the reaction products. Purification of the end product often requires additional time and is usually cumbersome. Notably, many common solvents used in the known commercial processes for preparing benzoxazimes pose toxicity risks, which may require expensive measures to eliminate, including the installation of costly solvent recovery systems or waste disposal.

Recently, Henkel Corporation (together with its parent corporation, Henkel AG & Co. KGaA, Dusseldorf, Germany) devised an improved synthesis for benzoxazines (See e.g. International Patent Application No. PCT/US2007/024519). That synthesis provides for: preparing a reaction mixture containing as reactants a phenolic component, a primary amine component, and an aldehyde component in an alkyl acetate solvent; and bringing the reactants and solvent to a temperature at which the reactants combine chemically and maintaining them at that temperature for a time sufficient to form a benzoxazine. And while this synthesis eliminated the need for the use of hazardous solvents such as toluene and dioxane, it would be desirable if even less volatile organic solvent could be employed to successfully produce benzoxazines.

A suitable reaction solvent should have at least some of the following properties. The reaction solvent should be inert to the reaction conditions and reagents, it should have an appropriate boiling point, and it should be easily removed at the end of the reaction. Solvents are usually classified into three general categories. "Polar protic" solvents which include water' "dipolar aprotic" solvents that include ethyl acetate; and "non-polar" solvents that include toluene.

Moreover, a solvent for use in a benzoxazine-forming reaction requires special considerations. For example, the use of organic solvents with diamine starting materials is known to lead to the formation of solids due to poor solubility. Indeed, Ishida, in Polymer, 50 (2009) 5940-5944 recognized that "[t]he synthesis of aromatic diamine-based benzoxazines is generally hampered by the poor solubility of many aromatic diamines in the preferred solvents used for benzoxazine preparation. Also, the formation of stable triaza network structure resulted from the condensation of diamine and formaldehyde suppresses the reaction to continue for benzoxazine formation. In addition, the other side condensation reactions are quite possible. All these factors led to a difficulty for aromatic diamine-based benzoxazine preparation."

The benzoxazine synthesis using toluene, a non-polar solvent, for instance, suffers from the high boiling point of toluene, even under vacuum. As a result, high temperature is needed to remove the toluene solvent from the benzoxazine product. However, since the benzoxazine product is somewhat volatile under these high temperature conditions, the toluene solvent cannot be completely separated from the benzoxazine product without removing the benzoxazine product as well. Moreover, the high temperatures required to remove the toluene also result in some degradation of the benzoxazine, along with some premature polymerization, ring opening, and increased viscosity.

The benzoxazine synthesis using ethyl acetate, a dipolar aprotic solvent, while an improvement over toluene, often shows the formation of undesirable solids, which may be removed by filtration, which can be undesirable. The filtrations can add time, labor, and cost, and also reduce the overall yield.

As such, an alternative solvent for the production of benzoxazines is desirable, whose properties include ease of product separation and low toxicity. The following solvent families have been determined to be unsuitable for the commercial synthesis of benzoxazines for the reasons given:

SUMMARY

The present invention is directed to methods for preparing benzoxazines comprising: (a) combining a phenol compound, a diamino compound, an aldehyde compound, water, and optionally an organic solvent, to form a reaction mixture; and (b) heating the reaction mixture for a time sufficient to form the benzoxazine. Benzoxazines formed by the described methods are also within the scope of the invention.

DETAILED DESCRIPTION OF ILLUSTRATIVE EMBODIMENTS

It has heretofore been surprisingly discovered that benzoxazines, both monomers and oligomers, can be produced using water as the reaction solvent. The methods of the invention optionally employ the use of an organic solvent. Water is considered by those skilled in the art to be the most desirable reaction solvent due to its innocuous nature. Nevertheless, until now, the formation of benzoxazines using water as the primary solvent has not been described.

Benzoxazines are known, per se, in the art and any known benzoxazines can be produced according to the methods of the invention. For example, benzoxazines of the invention may be embraced by the following monomer structure:

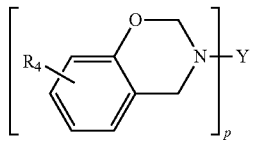

where p is 2, Y is selected from biphenyl, diphenyl methane, diphenyl isopropane, diphenyl sulfide, diphenyl sulfoxide, diphenyl sulfone, and diphenyl ketone, and $R_4$ is selected from hydrogen, halogen, alkyl and alkenyl.

The benzoxazine component may include the combination of multifunctional benzoxazines and monofunctional benzoxazines, or may be the combination of one or more multifunctional benzoxazines or one or more monofunctional benzoxazines.

Examples of monofunctional benzoxazines that may be prepared according to the invention may include those of the following structure:

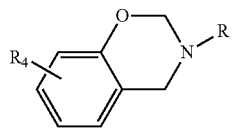

where R is alkyl, such as methyl, ethyl, propyls and butyls, or aryl with or without substitution on one, some or all of the available substitutable sites, and $R_4$ is selected from hydrogen, halogen, alkyl and alkenyl.

For instance, monofunctional benzoxazines may be embraced by the structure

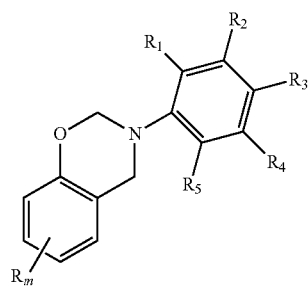

where in this case R is selected from alkyl, alkenyl, each of which being optionally substituted or includes one or more O, N, S, COO, and NHC=O, and aryl; m is 0-4; and $R_1$—$R_5$ are independently selected from hydrogen, alkyl, alkenyl, each of which being optionally substituted or interrupted by one or more O, N, S, C=O, COOH, and NHC=O, and aryl.

Specific examples of such a monofunctional benzoxazine are:

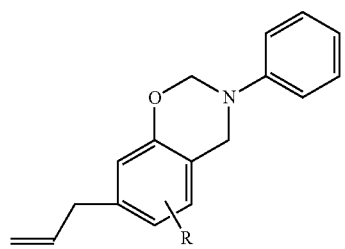

where R is as defined above; or

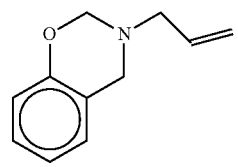

As used herein, "benzoxazine monomer" refers to single molecules of benzoxazines that include one or two benzoxazine subunits. One preferred benzoxazine monomer that can be prepared according to the methods described herein is:

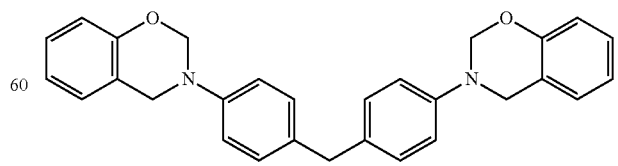

Other monomers can be prepared according to the described methods by modifying the amine, phenol, or aldehyde compound used in the benzoxazine reaction.

As used herein, "benzoxazine oligomer" refers to benzoxazine molecules that include repeating benzoxazine subunits. In typical embodiments of the invention, the number of repeating benzoxazine subunits is from 3 to about 20, preferably 3 to 10.

According to the invention the reactants are combined in water to form a reaction mixture. An organic solvent may optionally be added to the reaction mixture. It has been found that the addition of an organic solvent results in a dramatic reduction in the viscosity of the reaction mixture, thus facilitating the reaction progress and purification of the benzoxazine products. The organic solvent may be any organic solvent previously described for use in the synthesis of benzoxazines. Preferably, the organic solvent is an alkyl acetate ($CH_3C(O)OC_{1-10}$alkyl). In most preferred embodiment, the solvent is ethyl acetate.

When the organic solvent is used, it constitutes a minor amount of the reaction mixture. For example, when the organic solvent is used, it constitutes from about 1% to about 10%, by weight of the reaction mixture. Preferably, the organic solvent will constitute from about 1% to about 5%, by weight of the reaction mixture. More preferred is where the organic solvent constitutes from about 1% to about 3%, by weight of the reaction mixture. As used herein, "about" refers to plus or minus 10% of the recited value.

The reaction temperature employed to generate the benzoxazines will vary depending on the nature of the particular components used, but identification of an appropriate temperature is within the skill of those in the art. Generally, the reactions are run at temperatures above ambient temperature and below about 150° C. Preferably, the reaction temperature is about 100° C. or less with temperatures between about 50° C. and 100° C. being desirable. Preferred reaction temperatures are about 90° C.±5° C.

The methods of the invention are generally performed at atmospheric pressure. However, elevated pressure can be employed. Identification of such pressures is within the scope of those skilled in the art. For example, pressures up to about 100 psi can be employed for the methods of the invention.

The time of reaction will depend upon the nature of the reactants, as well as the reaction conditions. Those of skill in the art are capable of monitoring the reaction progress in order to determine when the reaction has proceeded sufficiently to produce desired amounts of benzoxazine. Commonly, a reaction time of about 15 to about 30 minutes is employed, although in some embodiments, the reaction may take up to about 10 hours. In other embodiments, the reaction may take up to about 4 or 5 hours.

The relative amounts of the reactants required will depend upon their chemical nature, e.g., the number of reactive groups taking part in the reaction. The stoichiometry is well within the skills of those conversant with the art, and the required relative amounts of reactants are readily selected, depending upon the functionality of the reacting compounds.

In some embodiments, it may be desirable to add a catalyst to the reaction mixture. Catalysts used for the formation of benzoxazines are generally basic in nature and include, for example, sodium hydroxide, potassium hydroxide, sodium carbonate, potassium carbonate, and the like.

After a period of time sufficient to form the benzoxazines, the reaction mixture may be poured onto cold water. This generally results in the precipitation of the benzoxazine product. The solid can be washed with water and then dried to produce the final product. This procedure is significantly less cumbersome and time consuming than procedures previously described for the synthesis of benzoxazines.

Alternatively, after a period of time sufficient to form the benzoxazines, the reaction mixture may be washed with water and/or aqueous base, for example, aqueous sodium hydroxide, potassium hydroxide, sodium carbonate, potassium carbonate, and the like.

The described methods can be employed to any of the benzoxazine processes previously described in the art. As such, the aldehyde compound used in the methods of the invention can be any aldehyde compound previously described for use in the formation of benzoxazines. Preferred aldehyde compounds include formaldehyde, e.g., formalin, paraformaldehyde, polyoxymethylene, as well as aldehydes having the general formula $R(CHO)_x$, where R is $C_0$-$C_{10}$ alkyl or cycloalkyl and x is, for example 1, 2, or 3, including mixtures of such aldehydes.

In addition, any phenol compounds previously described for use in the synthesis of benzoxazines can be used with the methods of the invention. For example, mono-functional phenols such as phenol, cresol, 2-bromo-4-methylphenol, 2-allylphenol, 1,4-aminophenol, or the like can be used. Suitable di-functional phenols include phenolphthalein, biphenol, 4-4'-methylene-di-phenol, 4-4'-dihydroxybenzophenone, bisphenol-A, 1,8-dihydroxyanthraquinone, 1,6-dihydroxnaphthalene, 2,2'-dihydroxyazobenzene, resorcinol, fluorene bisphenol, and the like. Suitable tri-functional phenols include 1,3,5-trihydroxy benzene and the like.

Any diamino compounds previously described for use in the synthesis of benzoxazines can be used with the methods of the invention. For example, suitable compounds include diamino alkylene compounds like methylene diamine, and diamino arylene compounds like phenylene diamines. For instance, U.S. Pat. No. 5,503,936 (Blyakhman) describes and claims curable modified epoxy resin compositions having an epoxy resin, a hardener or curing agent and 2.5 to 12.5% by weight of a compound represented by the following formula:

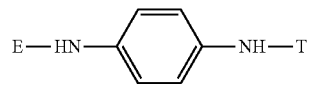

where E and T are $C_{5-12}$ alkyl, $C_{5-8}$ cycloalkyl, $C_{7-15}$ phenylalkyl, or $C_{6-10}$ aryl, with or without substitution by one or two $C_{1-4}$ groups. In addition, a number of suppliers including Flexsys America, Akron, Ohio, Sumitomo Chemical, Osaka, Japan, and Chemtura Corporation, Waterbury, Conn. sell phenylene diamine type anti-oxidants, which are promoted to retard oxidation, degradation, or pre-mature polymerization. U.S. Pat. No. 6,723,763 (Zhu) describes and claims compounds represented as within the following structure I:

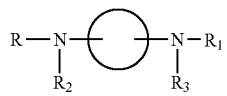

where R and $R^1$ may be the same or different and may be selected from $C_{1-12}$ alkyl, $C_{1-12}$ alkenyl, $C_{5-12}$ cyclo or bicycloalkyl, $C_{6-18}$ aryl, and derivatives thereof, $R^2$ and $R^3$ may be the same or different and may be selected from hydrogen, $C_{1-12}$ alkyl, $C_{1-12}$ alkenyl, $C_{5-12}$ cyclo or bicycloalkyl, $C_{6-18}$ aryl, and derivatives thereof and

is $C_{6-18}$ arylene, and derivatives thereof, and oxidized versions thereof.

Within this structure I are a variety of materials that may be used herein, for instance, the aromatic diamines represented below by structure II:

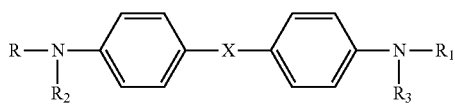

where X is NH, O or S, R, $R^1$, $R^2$, and $R^3$ are as described above for structure 1.

Also within the scope of the invention are those compounds within structure III:

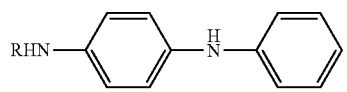

where R is as defined above for structure I. In addition, the oxidized version (shown below as structure IIIa) of structure III is also within the scone of the invention.

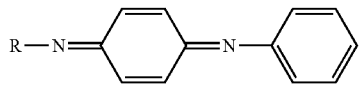

Within structure III is structure IIIb below, N-2-pentyl-N'-phenyl-p-phenylene diamine, which may also be used.

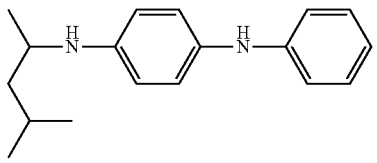

This phenylene diamine is believed to be available from Uniroyal Chemical Co., under the tradename FLEXZONE 7L.

Other specific examples within structure III include N-phenyl-N'-(1,3-dimethylbutyl)-p-phenylenediamine; N-phenyl-N'-isopropyl-p-phenylenediamine; N-phenyl-N'-(1-methylheptyl)-p-phenylenediamine; N-phenyl-N'-cyclohexyl-p-phenylenediamine; mixed diaryl-p-phenylenediamines; N,N'-diphenyl-p-phenylenediamine; N,N'-di-beta-naphthyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N-phenyl-N'-p-toluenesulfonyl-p-phenylenediamine; N-phenyl-N'-alkyl-p-phenylenediamines; dialkyl-p-phenylenediamines; N,N'-bis(1-cyclohexyl-1-ethyl)-p-phenylenediamine; N,N'-di(sec-hexyl)-p-phenylenediamine; N-(1,3-dimethylbutyl)-N'-(1,4-dimethylpentyl)-p-phenylenediamine; N-(sec-hexyl)-N'-(sec-alkyl)-p-phenylenediamines; N,N-di(1,4-dimethylpentyl)-p-phenylenediamine; 2,4,6-tris(N-alkyl-p-phenylenediamino)-1,3,5-triazine; 6-ethoxy-1,2-dihydro-2,2,4-trimethylquinoline; and combinations thereof. See U.S. Pat. Nos. 5,252,737 (Stern); 4,297,269 (Merten); 5,126,385 (Wheeler); and 5,068,271 (Wheeler).

More specific materials within structure I further include those within structure IV:

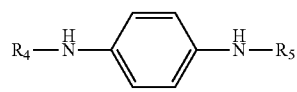

where $R^4$ and $R^5$ are $C_{5-12}$ alkyl, $C_{5-8}$ cycloalkyl, $C_{7-15}$ phenylalkyl, or $C_{6-10}$ aryl, with or without substitution by one or two $C_{1-4}$ groups.

In addition, the following may be used:

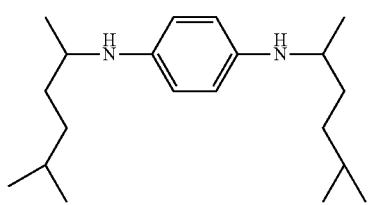

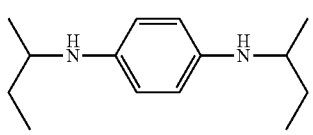

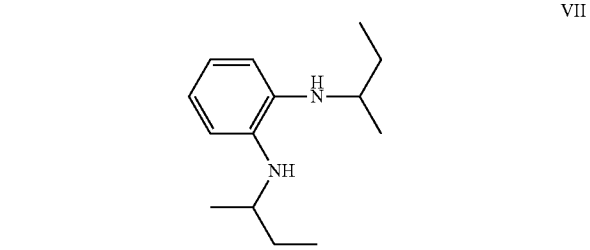

Structure V (UNILINK 7100) is N,N'-bis-4-(5-methyl-2-butyl)-p-phenylene diamine, structure VI (UNILINK 4100) is N,N'-bis-4-(2-butyl)-p-phenylene diamine, and structure VII (UNILINK 4102) is N,N'-bis-4-(2-methylpropyl)-o-phenylene diamine.

Other commercially available phenylene diamine cure accelerators include those available commercially from Plexysys under the tradename SANTOFLEX, such as SANTOFLEX 77PD and SANTOFLEX 715 PD, the latter of which being a mixture of

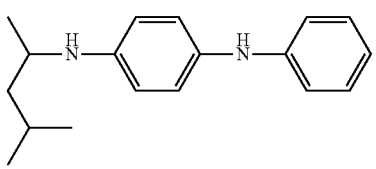

N-phenyl-N-(1,3-dimethylbutyl)-p-phenylenediamine (CAS No. 793-24-8) (also called SANTOFLEX 6PPD and FLEXZONE 7),

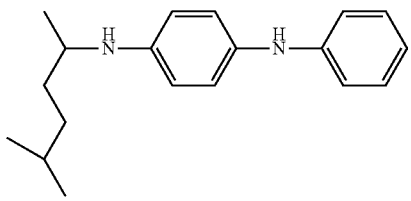

N-phenyl-N-(1,4-dimethylpentyl)-p-phenylenediamine (CAS No. 3081-01-4), and

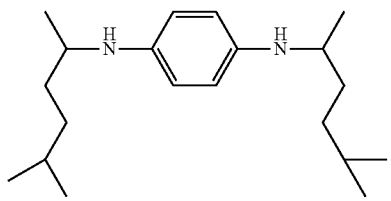

N,N'-bis(1,4-dimethylpentyl)-p-phenylene diamine (CAS No. 3081-14-9) (also called FLEXZONE 4L and SANTOFLEX 77PD).

The commercially available phenylene diamines may be obtained under one or more of the following tradenames: SUMILIZER from Sumitomo, such as BPA, BPA-M1, 4A, and 4M, and UOP from Crompton, such as UOP 12, UOP 5, UOP 788, UOP 288, UOP 88, UOP 26, UOP 388, UOP 588, UOP 36 and UOP 688.

In addition, compounds having an enamine unit formed from a carbocyclic ring having at least 5 ring atoms defined as those within the following structure VIII:

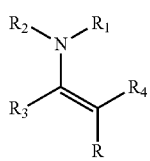

where R, $R^1$ and $R^2$ are each independently selected from alkyl, alkenyl, cycloalkenyl or aryl and substituted versions thereof, or taken together form a saturated or unsaturated ring with or without interruption by a heteroatom and with or without substitution and wherein at least one of $R^1$ or $R^2$ is H; $R^3$ and $R^4$ are each independently selected from —C(=X)—$R^5$ or Ar, where $R^5$ is alkyl, cycloalkyl, alkenyl, cycloalkenyl and aryl and substituted versions thereof, and Ar is an aromatic ring, and X is O, S, $NR^6$, $CR^7R^8$, or $CR^7NR^1R^2$, where $R^6$, $R^7$ or $R^8$ are each independently selected from alkyl, alkenyl, cycloalkenyl or aryl and substituted versions thereof, and at least one of $R^3$ and $R^4$ is —C(=X)—$R^5$ with X being $NR^6$, or $CR^7NR^1R^2$ and $R^1$ and $R^2$ are each independently as defined above. For instance,

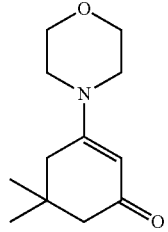

A

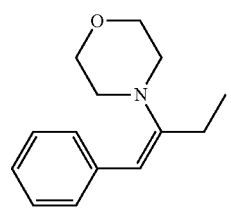

B

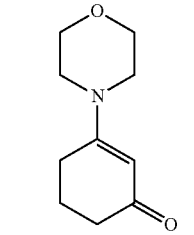

C

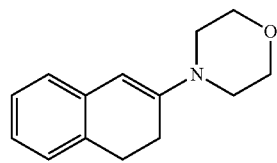

D

Other compounds include those from Huntsman Corporation, Houston, Tex., under the JEFFAMINE tradename, such as JEFFAMINE D-230, JEFFAMINE D-400, JEFFAMINE D-2000, JEFFAMINE T-403, JEFFAMINE ED-600, JEFFAMINE ED-900, JEFFAMINE ED-2001, JEFFAMINE EDR-148, JEFFAMINE XTJ-509, JEFFAMINE T-3000, JEFFAMINE T-5000, and combinations thereof.

Where a range of numerical values is recited herein, unless otherwise stated, the range is intended to include the endpoints thereof, and all integers and fractions within the range. It is not intended that the scope of the invention be limited to the specific values recited when defining a range. Moreover, all ranges set forth herein are intended to include not only the particular ranges specifically described, but also any combination of values therein, including the minimum and maximum values recited. Similarly, when values are expressed as approximations by use of the antecedent "about", it will be understood that the particular value forms another embodiment.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present disclosure, suitable methods and materials are described herein. All publications, patent applications, patents, and other references mentioned herein are incorporated by reference in their entirety, unless a particular passage is cited. In addition, the materials, methods, and examples are illustrative only and not intended to be limiting.

EXAMPLES

Example 1

6 grams (0.2 mol) of paraformaldehyde, 20 ml of ethanol, 0.1 grams of NaOH were reacted at 40° C. for 1 hour until the solution became clear. The mixture was cooled to 14° C. 20 ml of toluene and 9.98 grams (0.05 mol) of MDA were added and reacted for 1 hour at 15° C. Then 20 ml of toluene and 9.4 grams (0.1 mol) of phenol was added and the mixture was heated to 80° C. and refluxed for 5 hours. After cooling, the phases were allowed to separate. The upper water layer was removed. A light-yellow Benzoxazine-toluene solution was obtained. The ring closure percentage is >70%. (See CN94111852.5

Example 2

52 g of phenol, 55 g of MDA, 39 g of paraformaldehyde, 234 g of water, and 10 g of ethyl acetate were charged into a reactor vessel at room temperature. A small amount of catalytic base (NaOH) was added and the reaction mixture was maintained at a temperature of 90-95° C. for 4 hours. Approximately 60% by weight water and 3% by weight ethyl acetate are thus being used. The crude product was poured into cold water and precipitated into powder form. The resulting powder was rinsed with warm water several times and dried in a vacuum oven. Analysis: Monomer 33.2%; phenol 1.1%; ring closure 77%; volatile 0.57%; DSC onset 202° C.; DSC peak 223° C.

Structure of Monomer:

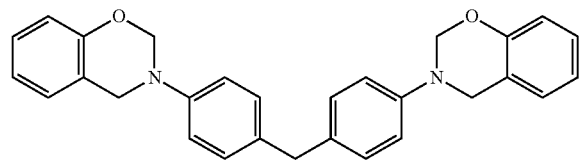

Example 3

95 g of paraformaldehyde, 150 g of MDA and 211 g of water were charged into a reactor vessel at room temperature. The reaction was maintained at room temperature for a period of 3 hours, using a small amount of catalytic base (NaOH) as catalyst. Then 30 g of ethyl acetate was added and the mixture was gently heated to 55° C. 138 g of phenol was charged and the reaction was kept at 85-90° C. for 4 hours. Approximately 34% water and 5% by weight ethyl acetate are thus being used. The crude product was poured into cold water and precipitated into powder form. The resulting powder was rinsed with warm water several times and dried in a vacuum oven. Analysis: Monomer 40.5%; phenol 1.45%; ring closure 80%; volatile 0.92%; DSC onset 211° C.; DSC peak 226° C.

Structure of Monomer:

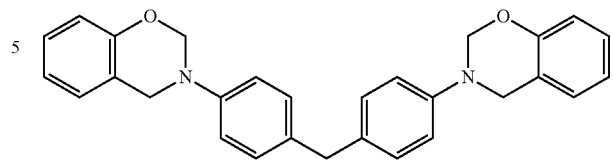

What is claimed:
1. A method for preparing a 1,3-benzoxazine comprising:
   (a) combining a phenol compound, a diamino compound, an aldehyde compound, and water, to form a reaction mixture; and
   (b) heating the reaction mixture for a time sufficient to form the benzoxazine.
2. The method of claim 1, wherein the reaction mixture further comprises an organic solvent.
3. The method of claim 2, wherein the amount of organic solvent is from about 1% to about 10%, by weight of the reaction mixture.
4. The method of claim 2, wherein the amount of organic solvent is from about 1% to about 5%, by weight of the reaction mixture.
5. The method of claim 2, wherein the amount of organic solvent is from about 1% to about 3%, by weight of the reaction mixture.
6. The method of claim 2, wherein the organic solvent is an alkyl acetate.
7. The method of claim 2, wherein the organic solvent is ethyl acetate.
8. A method for preparing a 1,3-benzoxazine comprising:
   (a) combining a phenol compound, a diamino compound, an aldehyde compound, and water to form a reaction mixture; and
   (b) heating the reaction mixture for a time sufficient to form the benzoxazine, wherein the reaction mixture further comprises a catalyst.
9. The method of claim 8, wherein the catalyst is a base.
10. The method of claim 9, wherein the base is sodium hydroxide, potassium hydroxide, sodium carbonate, potassium carbonate, or a mixture thereof.
11. The method of claim 1, further comprising the step of pouring the reaction mixture onto water after step (b).
12. The method of claim 1, further comprising the step of washing the reaction mixture of step (b) with aqueous base.
13. The method of claim 1, further comprising the step of washing the reaction mixture of step (b) with water.
14. A method for preparing a 1,3-benzoxazine comprising:
   (a) combining a phenol compound, a diamino compound, an aldehyde compound, and water to form a reaction mixture; and
   (b) heating the reaction mixture for a time sufficient to form the benzoxazine, wherein the reaction mixture is heated to a temperature of 100° C. or less.
15. The method of claim 1, wherein the reaction mixture is heated to a temperature of 90° C.±5° C.
16. The method of claim 1, wherein the time sufficient to form the benzoxazine is five hours or less.
17. The method of claim 1, wherein the phenol compound is phenol, cresol, 2-bromo-4-methylphenol, 2-allyphenol, 1,4-aminophenol, phenolphthalein, biphenol, 4-4'-methylene-di-phenol, 4-4'-dihydroxybenzophenone, bisphenol-A,

1,8-dihydroxyanthraquinone, 1,6-dihydroxnaphthalene, 2,2'-dihydroxyazobenzene, resorcinol, fluorene bisphenol, or 1,3,5-trihydroxy benzene.

18. The method of claim 1, wherein the aldehyde compound is formaldehyde, paraformaldehyde, or polyoxy.

19. A 1,3-benzoxazine produced by the method of claim 1.

20. The method of claim 1, wherein the benzoxazine may be embraced by one or more of the following structures:

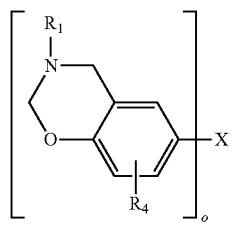

wherein o is 1-4, X is selected from direct bond (when o is 2), alkyl (when o is 1), alkylene (when o is 2-4), carbonyl (when o is 2), thiol (when o is 1), thioether (when o is 2), sulfoxide (when o is 2), and sulfone (when o is 2), $R_1$ is selected from hydrogen, alkyl, alkenyl and aryl, and $R_4$ is selected from hydrogen, halogen, alkyl and alkenyl; or

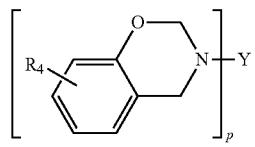

wherein p is 2, Y is selected from biphenyl (when p is 2), diphenyl methane (when p is 2), diphenyl isopropane (when p is 2), diphenyl sulfide (when p is 2), diphenyl sulfoxide (when p is 2), diphenyl sulfone (when p is 2), and diphenyl ketone (when p is 2), and $R_4$ is selected from hydrogen, halogen, alkyl and alkenyl.

* * * * *